US010125343B2

(12) United States Patent
Faustino Canadas et al.

(10) Patent No.: US 10,125,343 B2
(45) Date of Patent: Nov. 13, 2018

(54) ROTATIONAL DUAL CHAMBER BIOREACTOR: METHODS AND USES THEREOF

(71) Applicant: ASSOCIATION FOR THE ADVANCEMENT OF TISSUE ENGINEERING AND CELL BASED TECHNOLOGIES AND THERAPIES, Braga (PT)

(72) Inventors: Raphael Faustino Canadas, Guimaraes (PT); Joaquim Miguel Antunes De Oliveira, Braga (PT); Alexandra Margarida Pinto Marques, Porto (PT); Rui Luis Goncalves Dos Reis, Porto (PT)

(73) Assignee: ASSOCIATION FOR THE ADVANCEMENT OF TISSUE ENGINEERING AND CELL BASED TECHNOLOGIES AND THERAPIES—A4TEC, Braga (PT)

( * ) Notice: Subject to any disclaimer, the term of this patent is extended or adjusted under 35 U.S.C. 154(b) by 254 days.

(21) Appl. No.: 14/775,235

(22) PCT Filed: Mar. 13, 2014

(86) PCT No.: PCT/IB2014/059740
§ 371 (c)(1),
(2) Date: Sep. 11, 2015

(87) PCT Pub. No.: WO2014/141136
PCT Pub. Date: Sep. 18, 2014

(65) Prior Publication Data
US 2016/0024453 A1    Jan. 28, 2016

(30) Foreign Application Priority Data
Mar. 13, 2013  (PT) .......................... 106836

(51) Int. Cl.
*C12M 3/04* (2006.01)
*C12M 3/00* (2006.01)
(Continued)

(52) U.S. Cl.
CPC ............ *C12M 27/10* (2013.01); *C12M 21/08* (2013.01); *C12M 23/12* (2013.01); *C12M 23/34* (2013.01);
(Continued)

(58) Field of Classification Search
CPC ...... C12M 27/10; C12M 41/42; C12M 25/06; C12M 25/14; C12M 35/08; C12M 35/04; C12M 21/08; C12M 23/34; C12M 23/12
See application file for complete search history.

(56) References Cited

U.S. PATENT DOCUMENTS 5,602,028 A * 2/1997 Minchinton ........... C12M 25/02
                                                    210/615
7,604,987 B2   10/2009 Hutmacher et al.
(Continued)

FOREIGN PATENT DOCUMENTS

CN    101899393 A    12/2010
CN    102796664 A    11/2012
(Continued)

OTHER PUBLICATIONS

International Search Report dated Jul. 17, 2014 for Application No. PCT/IB2014/059740 and English translation.

*Primary Examiner* — Michael L Hobbs
(74) *Attorney, Agent, or Firm* — Lucas & Mercanti, LLP

(57) ABSTRACT

A rotational dual chamber bioreactor for cell culture in bi- and multi-layered scaffolds, in the context of tissue engineering (TE) and regenerative medicine strategies is disclosed, which comprises at least two dual culture chambers, a multiposition magnetic stirrer plate, and at least two flow
(Continued)

pumps coupled to a monitor device to register biochemical parameters such as pH, $pO_2$, glucose and urea sensors and physical parameters like pressure. A central barrier, with a hole to insert the bilayer scaffold, is used to culture cells with different conditions in each compartment of the chamber, avoiding medium exchange. Each chamber can rotate 180° (horizontal), which is promoted by magnetic stirrers, the multiposition stirrer plate is adapted dimensionally to the culture plate dimensions and also allows 180° vertical rotation. Each dual chamber has detachable caps for the top and the bottom chambers, the top cap to compress the scaffold thereby providing compressive stimulus with torsion simultaneously.

8 Claims, 5 Drawing Sheets

(51) Int. Cl.
*C12M 1/32* (2006.01)
*C12M 1/00* (2006.01)
*C12M 1/12* (2006.01)
*C12M 1/42* (2006.01)
*C12M 1/34* (2006.01)

(52) U.S. Cl.
CPC .......... *C12M 25/06* (2013.01); *C12M 25/14* (2013.01); *C12M 35/04* (2013.01); *C12M 35/08* (2013.01); *C12M 41/42* (2013.01)

(56) References Cited

U.S. PATENT DOCUMENTS

| | | |
|---|---|---|
| 2006/0141623 A1 | 6/2006 | Smith et al. |
| 2006/0199260 A1* | 9/2006 | Zhang ............... B01F 13/0059 435/293.1 |
| 2012/0035742 A1 | 2/2012 | Vunjak-Novakovic et al. |
| 2012/0183987 A1 | 7/2012 | Gevaert et al. |
| 2014/0030762 A1 | 1/2014 | Deplano et al. |

FOREIGN PATENT DOCUMENTS

| | | |
|---|---|---|
| CN | 203269948 U | 11/2013 |
| EP | 1990402 A1 | 11/2008 |
| EP | 2151491 A2 | 2/2010 |
| EP | 2236597 A1 | 10/2010 |
| WO | 2007012071 A1 | 1/2007 |
| WO | 2008098165 A2 | 8/2008 |
| WO | 2010040699 A1 | 4/2010 |
| WO | 2010064943 A1 | 6/2010 |
| WO | 2012173074 A2 | 12/2012 |
| WO | 2013103306 A1 | 7/2013 |

* cited by examiner

ROTATIONAL DUAL CHAMBER BIOREACTOR: METHODS AND USES THEREOF

CROSS REFERENCE TO RELATED APPLICATION

This Application is a 371 of PCT/IB2014/059740 filed on Mar. 13, 2014 which, in turn, claimed the priority of Portuguese Patent Application No. 106836 filed on Mar. 13, 2013, both applications are incorporated herein by reference.

TECHNICAL FIELD

The present disclosure describes a rotational dual chamber bioreactor which is used in tissue engineering (TE) and regenerative medicine applications. The apparatus is automated and can be controlled for different flow rates, inducing different shear stress, as well as different rotational speeds in 180°, allowing for adjustable diffusion of culture medium into the scaffolds, flow perfusion, as well as a different stimulus induced by the rotational movement. This new bioreactor system enable a controlled and homogeneous culture of cells in bi- or multi-layered scaffolds, allowing for the potential development of composed/layered tissues together in vitro.

BACKGROUND

A bioreactor may refer to a device or system meant to seed cells onto scaffolds and grow cells or tissues, under specific biochemical and/or mechanical conditions, in the context of cell culture. Therefore tissue development is facilitated by bioreactors. In this context, bioreactors are devices engineered to deliver appropriate spatial and temporal nutrient transport that may also incorporate mechanical or other physical stimulation, in a well-defined and controlled environment. Bioreactors that provide well-defined and controllable environments are useful for fundamental studies to optimize tissue growth, and it can act as production units for large-scale tissue fabrication and bioprocesses. Bioreactor systems can provide reliable model systems for fundamental studies of cell biology and play a key role in improving the quality of engineered tissues.

Different bioreactors have been reported in the literature, including mixed flasks [Vunjak-Novakovic et al 1996], rotating vessels [Freed et al 1998; Freed et al, 2000], perfused cartridges [Carrier et al, 2002], and bioreactors with different mechanical stimulation [Altman et al, 2001; Altman et al, 2002].

Bichamber bioreactors and oscillating bioreactors have also been described for application in osteochondral (OC) TE [Wendt et al, 2003; Chang et al, 2004; Valonen et al, 2010].

The main limitation of the current bioreactors for OC TE is that the newly formed tissue(s) is not homogeneously distributed within the bilayered scaffolds [Chen et al, 2013]. Furthermore, there are no bioreactors adapted for bilayered scaffolds that support different culture medium for each layer of the bilayered constructs, allowing inducing rotatory stimulus, compression and vertical movement to avoid cell sedimentation and undesired OC tissue malformation, at the same time.

Several patents have been granted based in the use of bioreactors for different applications. The following examples should be taken into account by their relevance in the area of this invention:

US2006141623 (A1) patent of 23 Jun. 2006 describes systems, modules, bioreactor and methods for the automated culture, proliferation, differentiation, production and maintenance of tissue engineered products in a general way. However, this system description doesn't refer to double chamber (a chamber with two compartments), to rotating movements of each chambers independently nor to all system turning movement.

WO 2007/012071 of 25 Jan. 2007 refers to a bioreactor device, and a method and system for fabricating tissues and growing cells and tissues in the bioreactor device. The bioreactor device includes a bioreactor chamber for containing a sample, where sample growth in response to mechanical, electrical, and biofactor stimulation is monitored through one or more optical ports. Embedded sensors are provided for measuring fluid pressure, pH, temperature, and oxygen tension. The bioreactor device can receive different types of mechanical loadings, including fluid shear, hydrostatic pressure, matrix compression, and rotation. The system does not present a double chamber for bilayered structures.

WO Patent 2008/098165 of 14 Aug. 2008 refers to oscillating cell culture bioreactor. The bioreactor has a gas permeable, closed-loop chamber for cell or tissue culture, and an oscillating means for moving the gas permeable, closed-loop chamber bi-directionally along an axis horizontal to an axis normal to the closed-loop chamber to force convection of cells and fluid in the gas permeable, closed-loop chamber. The bioreactor optionally includes a tissue engineering scaffold, an inlet means, an outlet means, and integrated sensors. Another aspect provides a bioreactor having a plurality of gas permeable, closed-loop chambers for cell or tissue culture.

EP Patent 1990402 of 12 Nov. 2008 describes a bioreactor to apply mechanical forces as an anabolic stimulus. The invention describes a bioreactor designed to be used in the field of cytomechanics. The system comprises an electroactive polymer actuator, also known as artificial muscle, which is bonded to a deformable, water impermeable biocompatible substrate/matrix. This layered structure is the flexible membrane of the bioreactor.

U.S. Pat. No. 7,604,987 of 20 Oct. 2009 relates to a bioreactor presenting a chamber for containing cells or tissue cultures within a culture medium. The bioreactor also comprises a detector capable of detecting a change in one or more metabolites associated with growth of the cell or tissue cultures within the chamber and a chamber drive capable of rotating the chamber at a first speed about a first axis and a second speed about a second axis, the second axis being disposed at an angle relative to the first axis. In use, the magnitude of the first speed and the second speed are independently variable of each other. However, this bioreactor is composed just by one chamber for all structures samples, preventing co-culturing cells with two different media separately in each structure and each structure have no independent chamber container.

WO Patent 2010/040699 of 15 Apr. 2010 relates to multi-culture bioreactor system that can maintain stem cells and differentiated cell types in physically isolated environments but can allow biochemical communication between these cells. Despite the system allows the co-culture and biochemical interaction between several chambers, these different chambers are physically isolated, and consequently does not allow obtaining integrated bi- or multi-layered cultured scaffolds on individual optimized environments.

WO Patent 2010/064943 of 11 Jun. 2010 describes a bi-directional continuous perfusion bioreactor for tri-dimensional culture of mammal tissue substitutes. The bioreactor induces mechanical cellular stimuli by creating shear forces caused by the flow perfusion using different pressure gradients, controlled by two pumps, a vacuum and a peristaltic one, positioned within a circular flow system designed for the bioreactor and also through rotational engines positioned in specific locations. This bioreactor is able to grow tissues of large dimensions, through the control of the perfusion and flow gradient within the scaffolds, thereby obtaining both access of the nutrients to the interior and the removal of the metabolic products of the interior of the material.

EP Patent 2236597 A1 of 6 Oct. 2010 presents a high-throughput sensorized bioreactor for applying hydrodynamic pressure and shear stress stimuli on cell cultures. This hydrodynamic pressure is generated inside at least one culture chamber by means of variation of the mean distance, with a controlled speed, of a surface relative to the surface on which the culture is positioned and between which the culture medium is free to flow.

CN 101899393 (A) patent of 1 Dec. 2010 belongs to the field of bone tissue engineering and cell mechanics relating to a dynamic load and recirculating perfusion bioreactor, which comprises a main body, a sliding sleeve module and a three-dimensional culture cabin module. The invention comprises a piezoelectric ceramic that penetrates into the three-dimensional culture cabin through the hole. The moving end of the piezoelectric ceramic is connected with a loading rod and the culture cabin main body is also provided with a liquid inlet and a liquid outlet which are externally connected with a peristaltic pump. The bioreactor does not perform rotational movements nor is adapted for dual chamber.

EP Patent 2151491 A3 of 23 Nov. 2011 discloses a multichamber bioreactor, however this system has not rotational movement, which is a limitation regarding homogenization of culture, because cell sedimentation can occur by gravity.

CN102796664 patent of 28 Nov. 2011 is related with a human body ligament tissue engineering bioreactor that can perform tension/compression and two-way torsional multi-dimensional stress loading. Moreover, it can automatically detect the loosening condition of the bracket and perform bracket loosening on-line compensation; and has the characteristics of simple and compact structure and high use convenience. This bioreactor does not perform inversion of the culture chamber and is not applied to bilayered structures.

US2012035742 (A1) patent of 9 Feb. 2012 describes methods, devices and systems for bone tissue engineering using a bioreactor to culture human bone grafts. This bioreactor is composed by a unique chamber without rotating movements.

WO 2013103306 A1 patent of 11 Jul. 2013 refers to a bioreactor composed of watertight chamber and internal matrix for the generation of cellularized medical implants. The bioreactor's internal matrices and external chamber are simultaneously manufactured, preferably through a rapid prototyping process. The system is also characterized by an external chamber possessing a shape adapted to the shape of the implant to be cellularized (internal matrix) enabling a greater efficiency in the cellular colonization and culture of the implant. This bioreactor is not adapted to perform mechanical stimulus nor real time monitoring.

CN203269948 patent of 6 Nov. 2013 describes a device for tendon and tendon sheath in vivo co-culture construction. The device comprises a tissue engineering tendon and tendon sheath co-culture bioreactor, a control unit and a measuring unit, wherein the tissue engineering tendon and tendon sheath co-culture bioreactor comprises tissue engineering tendon and tendon sheath culture units and a pneumatic tendon sliding mechanism. The system comprises also monitoring sensors for pressure and flow. The system does not present different speed rotations for the several chambers.

US2014030762 (A1) of 30 Jan. 2014 relates to a bioreactor for cell culture on a three-dimensional structure, comprising one culture chamber, the inner walls of which form a vertical duct, with a diameter that widens regularly form the duct inlet to the duct outlet, means enabling the culture medium to flow in said vertical duct. The invention also relates to the advantageous use of these bioreactors in tissue engineering, for the production of tissue grafts, notably a bone or cartilage graft. This patent does not describe dual-chambers, rotational movements or bilayered structures culture.

SUMMARY

The present disclosure provides a rotational dual chamber bioreactor adapted for co-culture of cells in bi- or multi layered scaffolds. For the first time allows culturing in dual chamber developing homogeneous tissues with bi- or multi layered by applying rotational movement in horizontal and vertical axis. The horizontal movement with two or more different programmable speeds, ranging from zero to 0.12 sec/degrees at no load, can be applied independently for each dual chamber, which can be used as a mechanical stimulation over the cells cultured onto a scaffold placed in that chamber, while the vertical movement with a programmable delay of time is applied for all the dual chambers together to avoid cell sedimentation by gravity. This bioreactor, which also can induce different shear flows of two different culture mediums circulating in each chamber independently, coupling two or more different flow pumps to the bioreactor and it is useful for simultaneously developing different mature tissues in vitro, i.e. osteochondral tissues. Furthermore, a top plate can be attached, fitting the top caps of each dual chamber, providing automatic mechanical compression and torsion according with the rotational movement performed by each chamber. The programmed rotational movement will directly set the compression speed also.

Thus the present disclosure describes a bioreactor comprising a multiposition magnetic stirred plate on which are placed at least two dual chambers, a top plate fitting the top cap of each dual chamber and at least two independent flow pumps.

A preferred embodiment of the present invention the dual chambers are fixed to the stirred plate by magnetic attraction and the referred stirred plate has a rotational movement, which is horizontal and/or vertical rotational movement.

In another embodiment of the present invention, the horizontal rotational movement is applied independently for each dual chamber, ranging from 0° to 180°.

A preferred embodiment of the present invention, the rotational movement comprises two or more programmable speed scales ranging from zero to 0.12 sec/degrees.

In another embodiment of the present invention, the vertical rotational movement is applied to all the chambers together, ranging from 0° to 180°.

A preferred embodiment of the present invention, the dual chamber comprises a central barrier with a hole in which is inserted the multilayered scaffolds; independent culture medium entries and outputs; a magnet in the bottom of the chamber; compressible and/or detachable top caps; and microsensors to register biochemical and physical parameters.

In another embodiment of the present invention, the dual chamber is a dual culture chamber whose dimension is adapted to the culture plate dimension, preferably 38.4 mm in diameter and 17.5 mm in height.

It is also an objective of the present invention to describe the use of the above described bioreactor in medicine or regenerative medicine, in particular in the biotechnology, pharmaceutical industry, biology or tissue engineering fields.

It is a further object of this invention to describe the use of the above described bioreactor for the development of in vitro tissue models and tissue engineering of different organs, drug screening and/or to mimic the articular joint movement and other body mechanical stimuli.

GENERAL DESCRIPTION

The technology represents a more realistic bioreactor mimicking different physical stimuli. The system is adapted for multilayered scaffolds cultured with two different culture media. Furthermore, the bioreactor overcomes the static culture disadvantages since it is able to turn in 180° avoiding cell sedimentation, movement promoted by a servomotor.

In respect to the bioreactor dynamics, this system is projected to the dual chambers perform compression and torsion of the top cap over the scaffolds and consequently over the cells by adding the top plate to the system. These chambers are bi compartmentalized for bi- or multilayered scaffolds. Each chamber position can perform 180° horizontal stirring to mimic for example the articular joint movement and improving culture medium diffusion.

Moreover, the dual culture chambers present two independent culture medium entries and outputs, which permit induction of independent and different shear flows.

All of the pieces that compose the dual chambers are autoclavable. The stirrer plate is controlled by a keyboard linked to an arduino (Atmel®) and a LCD display. The arduino is also linked to a servo control module. The stirrer plate can also incorporate a wi-fi system to control the stirring at distance, using computer software.

The bioreactor presents the possibility of having a determined number of samples in an equal number of independent culture positions or chambers. These bi-compartmentalized chambers allow flowing of two different culture media, rotating independently with two or more different programmable speeds. Furthermore the entire system has 180° turning movement to avoid cell sedimentation promoted by the servomotor.

Regarding the data collection and friendly-user features, the dual chamber's size is adapted to meet the requirements of the user regarding the sizes of existing culture plates, and are placed by magnetic attraction, feature that facilitate the removal and replacement of the dual chambers, as well as the analysis of individual chambers without affecting the remaining chambers in culture.

The described technology can be used to develop different in vitro tissue models platforms that allows replacing or decreasing the animal models for scientific research and in the pharmaceutical field for drug screening and evaluation, decreasing the time consuming, the animal unnecessary use and the involved costs (drug discovery and testing and tissue engineered products development).

In the biotechnology, biology and tissue engineering fields, nowadays, the culture medium diffusion into 3D porous scaffolds is a challenge to be overcome in order to develop 3D tissue able to be used in the clinic. Applying the bioreactor technology like the Rotational Dual Chamber Bioreactor, this problem will be solved. Furthermore the technology under invention could mimic for example the articular joint movement contributing to be a platform to develop research on articular joints opening avenues to study disorders like Osteoarthritis or Osteoporosis.

Innovations, Advantages and Some Applications:
- Multiple and independent positions that can be stimulated by rotational movement up to 10 programmable speeds scales. This feature can be useful for two different goals: first the improvement of culture medium diffusion into the 3D culture scaffolds; secondly, it can simulate, for example, an articular movement performed by our joints, since the rotation is of 180° horizontally.
- All system can automatically turn 180° up and down in a specified delay of time.
  - Cell's sedimentation can occur in 3D cell culture. With this turning movement this will be avoided. Furthermore, if in a specific study the turning movement is not desirable this feature can be disabled.
- Dual Chambers adapted for 3D bilayered structures that can support the growth of two different cell lineages (or stem cells fate)
  - Nowadays, in tissue engineering and regenerative medicine field, the complexity of the developed structures to be implanted is increasing. There is also the need to mimic native tissues, such as the articular joint movement, for the appropriate development of in vitro tissue models for drugs screening. Thus, the goal is to develop more complex structures that can include two types of different tissue (for example, in the osteochondral for cartilage and bone). To obtain this, different cell lines or primary cultures (e.g., adult stem cells from different origin) need to be used and cultured together.
- Each one of the dual chambers can have different conditions and can be checked without interfering with the other chambers in culture
  - Cells co-culture could be improved, studying both cell lines secretome over time (under the effect of a specific drug).
- Allows the flow of two different culture media in the two parts of each dual chamber.
  - Interfaces of our body could be tested in a dynamic system, like for example blood-brain barrier.
  - Two different drugs could be applied flowing in the same Dual-chamber, or testing the diffusion between one and other compartment of each dual-chamber through a cell sheet.
  - Using the Rotational Dual-Chamber Bioreactor, the optimization of two different culture media used in co-cultures is definitely possible for two different tissues or cell lines growing simultaneously. The existing bioreactors allow 3D cultures but using only one specific culture medium.
- The bioreactor will be adapted to perform cyclic compression movements
  - In our body a lot of physical stimuli are interfering with our health. For example osteoarthritis is generated by chemical mediators but also by physical loadings. Applying this kind of pressure, models for this kind of disease can be created, allowing developing a more realistic platform for drug effect studies, avoiding the ethical and technical problems associated with animal models.

These are just few examples of some interesting applications possible with this bioreactor. Overviewing, we are presenting a new concept of bioreactor with a lot of variables that can be enabled and disabled independently, but all of them can contribute to have a more realistic, controlled, fast and accessible environment. The broader features of the presented bioreactor make it a valuable tool for studies from the fundamental science until the applied pharmaceutical and medical/surgical fields.

BRIEF DESCRIPTION OF THE DRAWINGS

Without intent to limit the disclosure herein, this application presents attached drawings of illustrated embodiments for an easier understanding.

DESCRIPTION OF PREFERRED EMBODIMENTS

Figure 1:
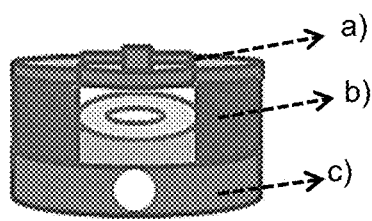
FIG. 1. Perspective view of the dual chamber (with open view for the inside), wherein a) is top cap of each dual chamber, b) represents the central part of the dual chamber where is comprised the bi-compartmentalization with the central hole for structure insertion and c) represents the bottom part adapted for insertion of a magnetic bar to fix the dual chamber to the stirred plate by magnetic attraction.
Figure 2:
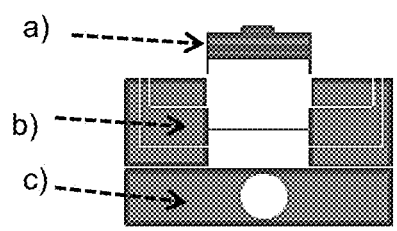
FIG. 2. Cross section of the dual chamber.
Figure 3:
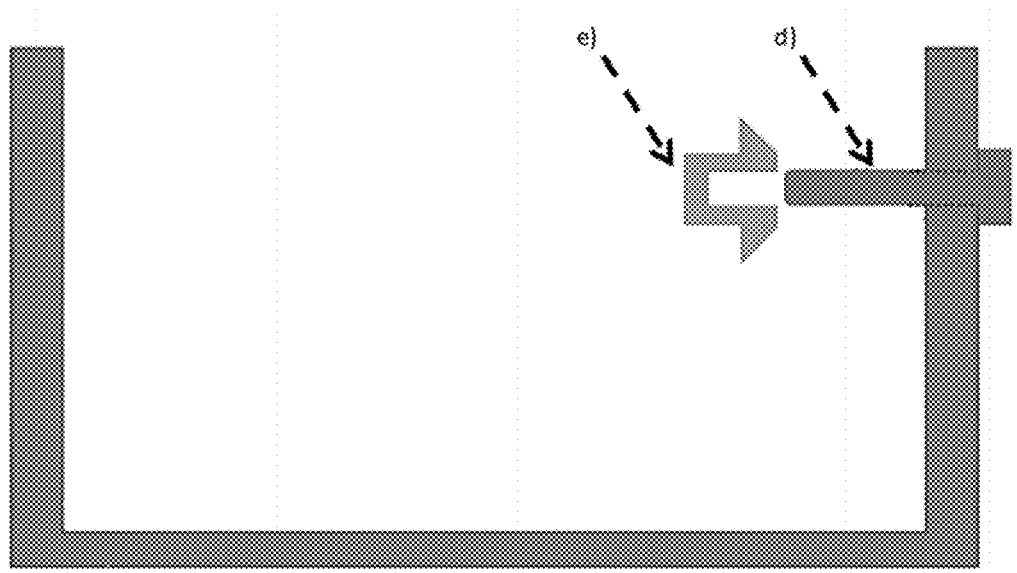
FIG. 3. Lateral view of the holder for the bioreactor, constituted by d) the screw of the support for fixing the stirred plate and e) fitting of the stirred plate.
Figure 4:
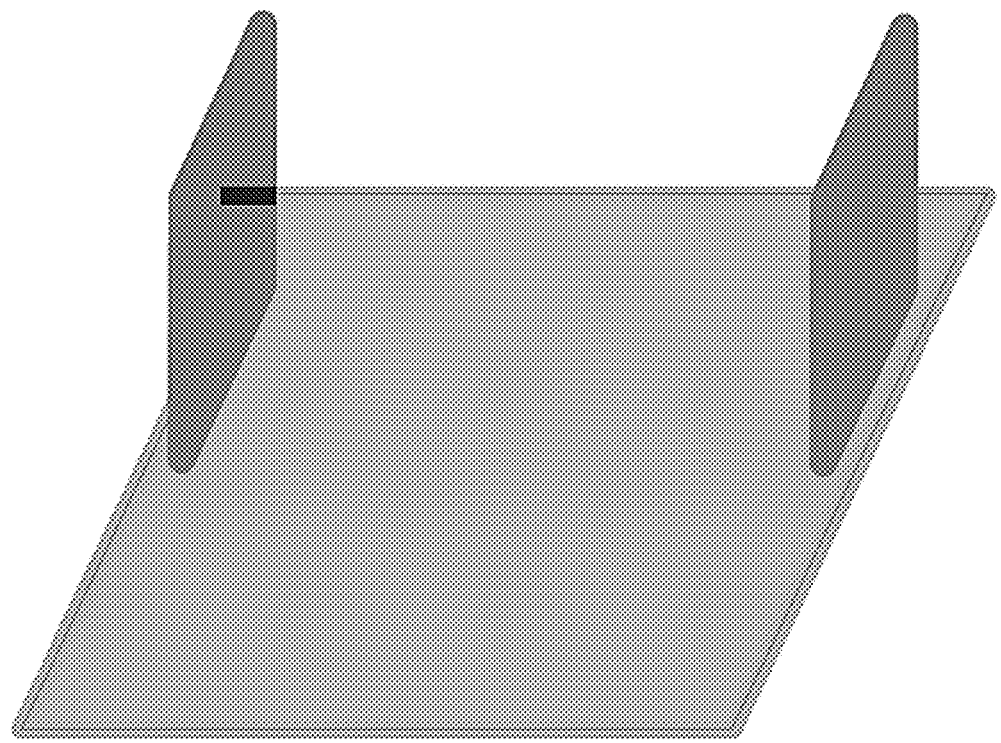
FIG. 4. Perspective view of the holder for the bioreactor
Figure 5:
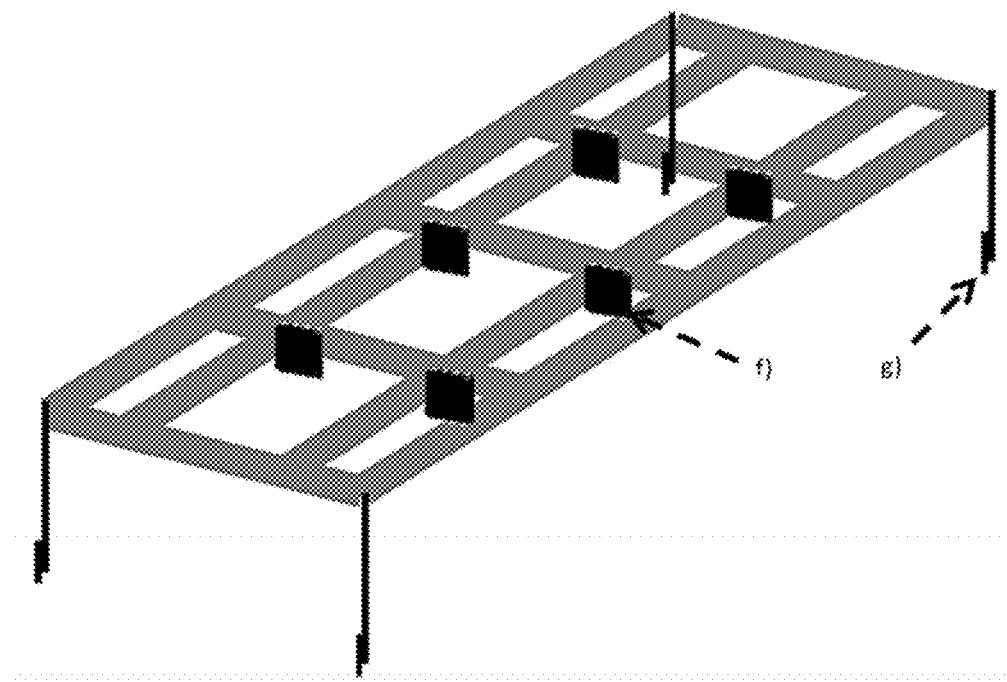
FIG. 5. Perspective view (from bottom) of the top plate to be used for allowing mechanical compression. The plate is comprises the following features: f) adapters to entry in the top caps of dual chambers and g) supports that are attached by elastic to the dynamic platform.
Figure 6:
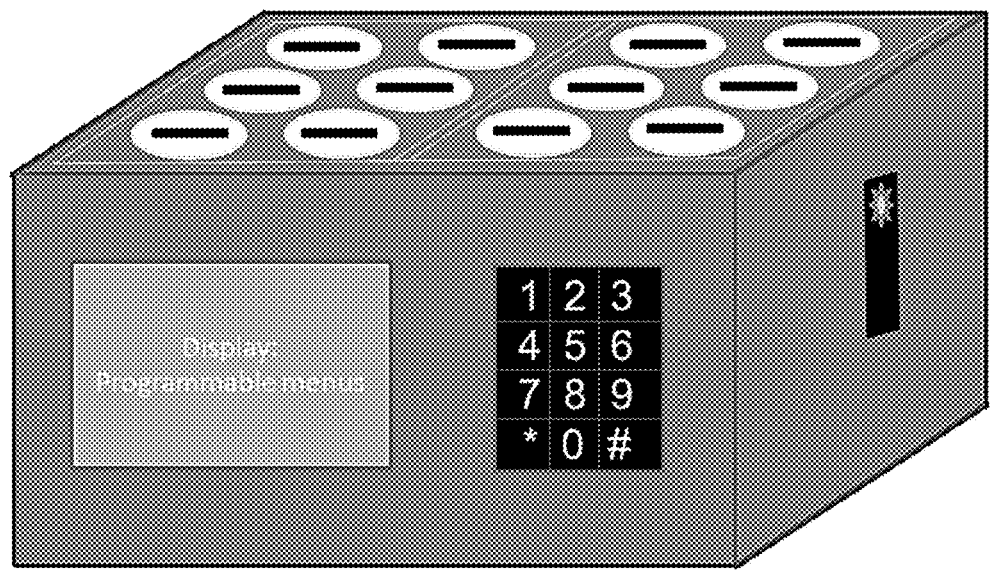
FIG. 6. Dynamic platform of the bioreactor that performs the rotating movements (horizontal and vertical). This platform is attached to and suspended by the holder.

This invention refers to a rotational dual chamber bioreactor that is composed by a set of dual culture chambers, a multiposition magnetic stirrer plate, and flow pump(s).

The dual culture chambers present two independent culture medium entries and outputs, which permit induction of independent and different shear flows, and a central separator with a hole for insertion of the scaffold, whereby there is integration of the two chambers. The dual chambers have a magnetic bar attached to the bottom part.

The multiposition magnetic stirrer plate with 12 positions adapted for two 6 well tissue culture plates, which control independent horizontal movement for each position and vertical movement for all the plate.

Rotational Dual Chamber Bioreactor:

The dual chamber bioreactor is composed by a stirrer plate, which can be rotated vertically until 180°. In addition, the stirrer plate have 12 positions where can be placed, by magnetic attraction, 12 dual chambers. Each one of the 12 positions can be independently controlled to rotate until 180° with 10 different speeds ranging from zero to 0.12 sec/degrees at no load.

Dual Culture Chambers:

The bioreactor can incorporate 12 dual culture chambers. The dual culture chambers have a central barrier with a hole to insert the bilayer scaffold. This kind of well serve to culture cells with different conditions in each chamber. The design of the dual culture chambers allows avoiding the mixture of the culture media. In the bottom part of the dual culture chamber is attached a magnetic bar to be attracted with the rotating position in the stirrer plate. Each chamber has detachable caps for the top and the bottom chambers. The top cap presents the possibly to compress the scaffold, allowing to test a compressive stimulus. The dual chambers have dimensions to adapt to commercial 6-well tissue culture plates (38.4 mm diameter, 17.5 mm height). This way, and being the top and bottom of the chambers detachable, the culture can be observed by microscopy. Microsensors can be added to the system to monitor several biochemical parameters, as oxygen tension, pH, temperature, or glucose and urea concentration and physical parameters like pressure. All of the pieces that compose the dual chambers are autoclavable.

Stirrer Plate:

The 12 multiposition stirrer plate is adapted dimensionally to two standard 6 well tissue culture plates. In each of the 12 positions can be inserted one of the dual culture chambers by magnetic attraction. In each position can rotate until 180° (horizontal), being the rotations per minute controlled independently. The rotation is promoted by magnetic stirring, having magnets performing the attraction between the bottom part of the well and the stirring position in the plate. Vertical 180° movement can also be applied for all the chambers together.

The stirrer plate is controlled by a keyboard linked to a LCD display. The system is coordinated by an arduino (Atmel®) synchronized with a servo control module. The stirrer plate can also incorporate a wi-fi system to control the stirring at distance, using computer software.

All of the system can be placed inside an incubator.

Osteochondral Tissue Development Using the Dual Chamber Rotational Bioreactor

To develop an OC analogue, which can be further use in as an in vitro 3D tissue model, undifferentiated adipose derived stem cells (ASCs) isolated from Fat Pad are cultured in a bilayered scaffold, aiming at in situ cell differentiation into chondrocyte and osteoblast-like cells. The bilayered scaffolds comprise the cartilage- and bone-like layers, which are composed of gellan gum (GG) and GG with dispersed hydroxyapatite (HAp) particles, respectively.

In vitro mature and homogeneous OC tissue formation is achieved by culturing ASCs within the GG-HAp/GG bilayered scaffold by means of using the dual chamber rotational bioreactor. An optimized chemical mediation is provided at each compartment of the dual chamber, i.e. in one compartment is provided the osteogenic medium and in the second compartment is provided the chondrogenic medium. Chondrogenic differentiation culturing cocktail is performed based on well-established protocols. Although osteogenic differentiation of ASCs can require additional Growth Factors, due to the presence of hydroxyapatite in the bone-like part of the scaffold, the conditions to maintain both cell types in co-culture needed to be optimized. The optimization, taking advantage of the dynamic culture system, accounts for the presence and the influence of osteogenic/chondrogenic mediators such as dexamethasone, L-ascorbic acid-2-phosphate, β-glycerophosphate, BMPs, FGF, platelet-derived GF and TGF-β.

Figure 7:
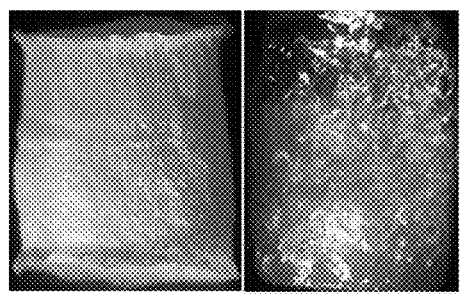
FIG. 7. Bilayered structures of Gellan gum-Gellan Gum/ Hydroxyapatite; on the right: hydrated and stained with Alizarin red. In Alizarin red stained structure, the bottom part was stained with red (opaque in image) because of the presence of Hydroxyapatite particles. The top and brighter part is related with Gellan gum transparent part.
Figure 8:
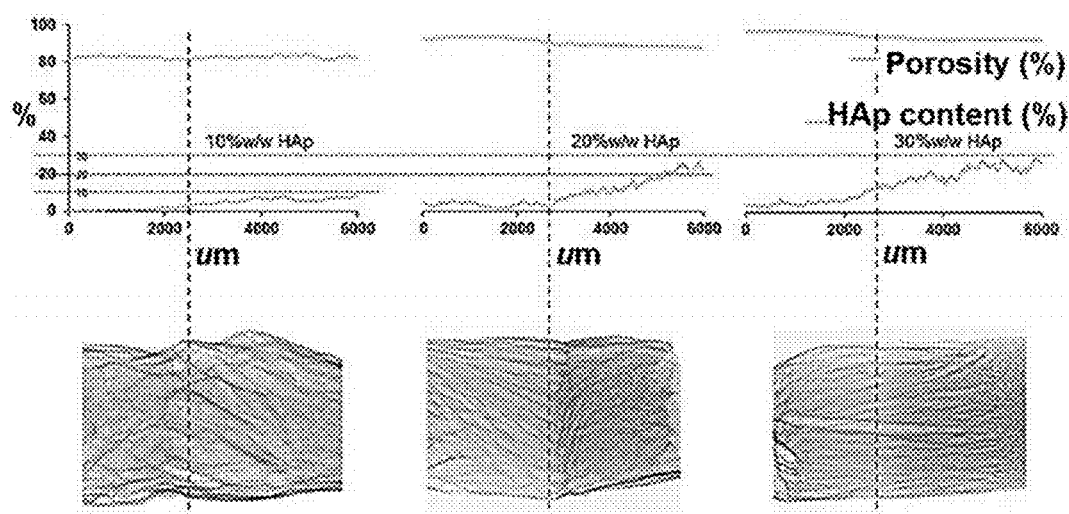
FIG. 8. Bilayered structures profile for Hydroxyapatite % distribution and porosity. Left part of each structure is related with Gellan gum part, and right part with Gellan gum with Hydroxiapatite particles.
Figure 9:
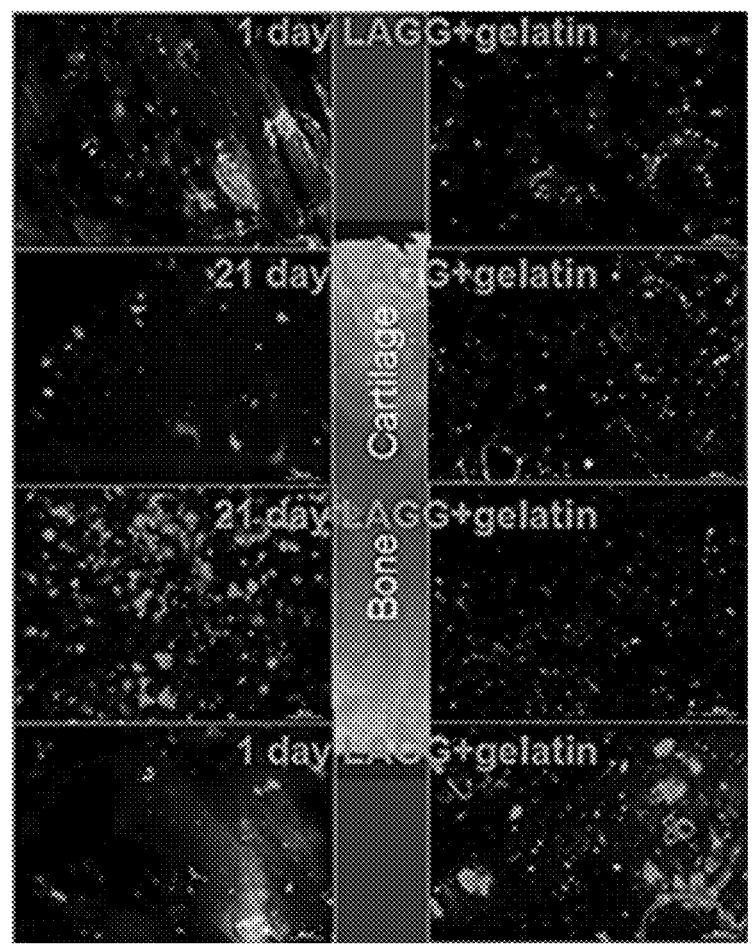
FIG. 9. Rabbit Adipose derived stem cells from Fat Pad cultured on bilayered structures with gelatin in composition. DAPI/phalloidin and live/dead staining's for cells at the time-points of 24 h and 21 days of culturing. On left, it is possible to observe the cells stained with Phalloidin (white parts in the image). On right, it is possible to observe the living healthy cells (white colour).

The mixture of the different culture medium is prevented due to the independent flow through the two compartments of the chamber. This maximizes the differentiation potential of the ASCs towards each lineage in the respective scaffold layers. The system characterized by the dual chamber rotational bioreactor and the produced living tissue aims to be used as a 3D in vitro OC model. These 3D tissue models make possible the continuous analysis of the growth factors production and allow culture conditions optimization, thus holding a great promise for application in tissue engineering and regenerative medicine, and screening of bioactive molecules or drugs (FIGS. 7, 8 e 9).

The present disclosure is of course not in any way restricted to the embodiments described and a person with ordinary skill in the art will foresee many possibilities to modifications thereof without departing from the basic idea of the invention as defined in the appended claims.

The following claims set out particular embodiments of the invention.

The invention claimed is:

1. A bioreactor comprising:
   a multiposition magnetic stirrer plate;
   at least two dual chambers removably fixed to the multiposition magnetic stirrer plate by magnetic attraction via at least one magnet, the dual chambers comprising a top chamber and a bottom chamber,
      wherein the top chamber is a bi-compartmentalized culture chamber and comprises a top detachable cap, and
      wherein the bottom chamber is a detachable base housing the at least one magnet, avoiding direct contact with the culture medium;
   at least two independent flow pumps; and
   a platform for housing the multiposition magnetic stirrer plate, the at least two dual chambers and the at least two independent flow pumps,
   wherein the multiposition magnetic stirrer plate comprises a servo motor to vertically rotate the multiposition magnetic stirrer plate with the dual chambers, and at least two servo motor corresponding to each of the at least two dual chambers to independently horizontally rotate each dual chamber, the at least two servo motors placed between the dual chambers and the multiposition magnetic stirrer plate, and
   wherein the at least one magnet removably fixes by magnetic attraction the at least two dual chambers to the multiposition magnetic stirrer plate.

2. The bioreactor according to claim 1, wherein the horizontal rotational movement ranges from 0° to 180°.

3. The bioreactor according to claim 2, wherein the rotational movement comprises two or more programmable speed scales ranging from zero to 0.12 sec/degrees.

4. The bioreactor according to claim 1, wherein the vertical rotational movement is applied to all dual chambers simultaneously.

5. The bioreactor according to claim 1, wherein the vertical rotational movement ranges from 0° to 180°.

6. The bioreactor according to claim 1, wherein the dual chamber further comprises:
   a central barrier with a hole in the bi-compartmentalized culture chamber wherein the multilayered scaffolds are inserted;
   independent culture medium entries and outputs;
   compressible and/or detachable top caps; and
   microsensors to register biochemical and/or physical parameters.

7. The bioreactor according to claim 6, wherein the dual chamber is a dual culture chamber whose dimension is adapted to the culture plate dimension, preferably 38.4 mm in diameter and 17.5 mm in height.

8. The bioreactor according to claim 1, further comprising a top plate comprising adapters configured to enter into the top detachable cap of the dual chambers and supports attached to the platform.

* * * * *